United States Patent

Oldfield et al.

[11] Patent Number: 5,317,101
[45] Date of Patent: May 31, 1994

[54] TRICYCLIC HETEROCYCLES

[75] Inventors: John Oldfield, Wilmslow; Howard Tucker, Macclesfield, both of England

[73] Assignee: Imperial Chemical Industries PLC, London, England

[21] Appl. No.: 950,706

[22] Filed: Sep. 25, 1992

[30] Foreign Application Priority Data

Sep. 27, 1991 [GB] United Kingdom ................ 9120640

[51] Int. Cl.$^5$ .................... C07D 267/18; A61K 31/55
[52] U.S. Cl. .................................... 540/488; 540/495; 540/521; 540/557; 540/551; 540/587
[58] Field of Search ............... 540/488, 495, 521, 557, 540/551, 587

[56] References Cited

U.S. PATENT DOCUMENTS

| 3,534,019 | 10/1970 | Coyne et al. | 540/551 |
| 3,624,104 | 11/1971 | Cusic et al. | 540/551 |
| 3,644,346 | 2/1972 | Cusic et al. | 540/551 |
| 3,917,649 | 11/1975 | Mueller | 540/551 |
| 3,989,719 | 11/1976 | Mueller | 540/551 |
| 3,992,375 | 11/1976 | Mueller | 540/551 |
| 4,559,336 | 12/1985 | Mueller | 540/551 |
| 4,559,337 | 12/1985 | Mueller | 540/551 |
| 4,728,735 | 3/1988 | Belanger et al. | 540/488 |

FOREIGN PATENT DOCUMENTS

| 0193822 | 9/1986 | European Pat. Off. | 540/551 |
| 0218077 | 4/1987 | European Pat. Off. | 540/551 |
| 0447857 | 9/1991 | European Pat. Off. | 540/551 |
| 61-17663 | 7/1986 | Japan | 540/522 |
| 1170322 | 11/1969 | United Kingdom | 540/488 |
| 1192016 | 5/1970 | United Kingdom | 540/455 |
| 1522003 | 8/1978 | United Kingdom | 540/551 |

OTHER PUBLICATIONS

Japanese J6 1167 650-A-Abstract in Derwent Publications Limited 80134 Jul. 29, 1986.

*Primary Examiner*—Robert T. Bond
*Attorney, Agent, or Firm*—Cushman, Darby & Cushman

[57] ABSTRACT

The invention relates to tricyclic heterocycles of the formula I

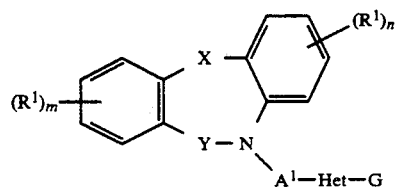

wherein
X is oxy, thio, sulphinyl, sulphonyl, amino, (1-4C)alkylamino or methylene;
Y is carbonyl or methylene;
each $R^1$ includes hydrogen, halogeno and various other substituents;
each of m and n is 1 or 2;
$A^1$, alkylene, alkenylene or alkynylene;
Het is a 5 or 6 membered heteroaryl group optionally bearing particular substituents; and
G is carboxy, 1H-tetrazol-5-yl or a group of the formula:

—CONH—SO$_2$R$^2$ wherein $R^2$ is (1-4C)alkyl, benzyl or phenyl;
and pharmaceutically-acceptable salts thereof, which possess anti-hyperalgesic properties. The invention also relates to processes for the manufacture of said tricyclic heterocycles; and to novel pharmaceutical compositions containing them.

5 Claims, No Drawings

TRICYCLIC HETEROCYCLES

This invention relates to novel tricyclic heterocycles, or pharmaceutically-acceptable salts thereof, which possess useful pharmacological properties. More particularly the compounds of the invention may be used to counteract mild or moderate pain by virtue of their anti-hyperalgesic properties. The invention also relates to processes for the manufacture of said tricyclic heterocycles, or pharmaceutically-acceptable salts thereof; to novel pharmaceutical compositions containing them; and to the use of said compounds in the production of an anti-hyperalgesic effect in the human or animal body.

As stated above the compounds of the invention may be used to counteract mild to moderate pain such as the pain associated with inflammatory conditions (such as rheumatoid arthritis and osteoarthritis), postoperative pain, post-partum pain, the pain associated with dental conditions (such as dental caries and gingivitis), the pain associated with burns (such as sunburn) and the pain associated with sports injuries and sprains. In many of these conditions a hyperalgesic state is present, i.e. a condition in which a warm-blooded animal is extremely sensitive to mechanical or chemical stimulation which would normally be painless. Thus a hyperalgesic state is known to accompany certain physical injuries to the body, for example the injury inevitably caused by surgery. Hyperalgesia is also known to accompany certain inflammatory conditions in man such as arthritic and rheumatic disease. It is known that low doses of prostaglandin $E_1$ or prostaglandin $E_2$ (hereinafter $PGE_1$ and $PGE_2$ respectively) can induce the hyperalgesic state. Thus, for example, a long-lasting hyperalgesia occurs when $PGE_1$ is infused in man and, in particular, the co-administration of $PGE_1$ with a further chemical stimulant such as bradykinin causes marked pain. Thus it is believed that prostaglandins such as $PGE_1$ and $PGE_2$ act to sensitise pain receptors to mechanical or chemical stimulation.

These undesirable effects of the arachidonic acid metabolite $PGE_2$ could be ameliorated if its production could be inhibited. It is believed that such an inhibitory effect, by virtue of inhibition of the enzyme cyclooxygenase, contributes to the mode of action of the non-steroidal anti-inflammatory drugs or NSAIDS such as aspirin and indomethacin. Unfortunately the effective pain relief afforded by such agents is often accompanied by undesirable side effects such as gastrointestinal irritation.

An alternative way of ameliorating the effects of $PGE_2$ is to use an agent capable of antagonising its sensitising effects at the receptor or receptors responsible for mediating hyperalgesia. Certain compounds which possess such prostaglandin-antagonist properties are known. Thus it is known that various 10,11-dihydrodibenzo[b,f][1,4]-oxazepine-10-carboxylic acid hydrazides are $PGE_2$ antagonists and these are stated to possess analgesic properties [European Patent Application No. 0218077].

We have now found that certain novel tricyclic heterocycles which possess a very different side-chain to the carboxylic acid hydrazide side-chain of the compounds disclosed in EP 0218077 are effective $PGE_2$ antagonists. Thus such compounds are of value in the treatment of mild or moderate pain and in the antagonism of the hyperalgesic state which, for example, accompanies inflammatory conditions such as rheumatoid arthritis and osteoarthritis.

The compounds of the invention also possess anti-inflammatory, anti-pyretic and anti-diarrhoeal properties by virtue of antagonism of the effects of $PGE_2$.

According to the invention there is provided a tricyclic heterocycle of the formula I (set out hereinafter) wherein X is oxy, thio, sulphinyl, sulphonyl, imino, (1-4C)alkylimino or methylene, the last named group optionally bearing one or two (1-4C)alkyl groups;

Y is carbonyl or methylene, the latter group optionally bearing one or two (1-4C)alkyl groups;

each $R^1$ which may be the same or different, is selected from hydrogen, halogeno, trifluoromethyl, nitro, cyano, hydroxy, amino, (1-4C)alkyl, (1-4C)alkoxy, (1-4C)alkylthio, (1-4C)alkylsulphinyl, (1-4C)alkylsulphonyl, (1-4C)alkylamino and di-(1-4C)alkylamino;

m and n, which may be the same or different, is the integer 1 or 2;

$A^1$ is (1-4C)alkylene, (3-4C)alkenylene or (3-4C)alkynylene;

Het is a 5- or 6-membered heteroaryl moiety containing up to 2 heteroatoms selected from nitrogen, oxygen and sulphur, and which may optionally bear one substituent selected from halogeno, trifluoromethyl, nitro, cyano, hydroxy, amino, (1-4C)alkyl and (1-4C)alkoxy; and G is carboxy, 1H-tetrazol-5-yl or a group of the formula:

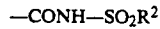

wherein $R^2$ is (1-4C)alkyl, benzyl or phenyl, the latter two of which may optionally bear one or two substituents selected from halogeno, trifluoromethyl, nitro, cyano, hydroxy, (1-4C)alkyl and (1-4C)alkoxy;

or when G is carboxy an in-vivo hydrolysable ester thereof or an amide thereof;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However, references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more asymmetric carbon atoms, the invention includes in its definition of active ingredient any such optically active or racemic form which possesses anti-hyperalgesic properties. The synthesis of optically active forms may be carried out by standard techniques of organic chemistry well known in the art, for example by synthesis from optically active starting materials or by resolution of a racemic form. Similarly, anti-hyperalgesic properties may be evaluated using the standard laboratory techniques referred to hereinafter.

Suitable values for the generic terms referred to above include those set below.

A suitable value for the (1-4C)alkyl group when X is (1-4C)alkylimino, or X or Y is methylene which bears one or two (1-4C)alkyl groups is, for example, methyl, ethyl, propyl or isopropyl.

A suitable value for each $R^1$, which may be the same or different, when it is halogeno is, for example, fluoro, chloro or bromo; when it is (1-4C)alkyl is, for example, methyl, ethyl, propyl, isopropyl, butyl, isobutyl, sec-butyl or tert-butyl; when it is (1-4C)alkoxy is, for example, methoxy, ethoxy, propoxy or isopropoxy; when it is (1-4C)alkylthio is, for example, methylthio, ethylthio, propylthio or isopropylthio; when it is (1-4C)alkylsulphinyl is, for example, methylsulphinyl, ethylsulphinyl, propylsulphinyl or isopropylsulphinyl; when it is (1-4C)alkylsulphonyl is, for example, methylsulphonyl, ethylsulphonyl, propylsulphonyl or isopropylsulphonyl; when it is (1-4C)alkylamino is, for example, methylamino, ethylamino, propylamino or isopropylamino; and when it is di-(1-4C)alkylamino is, for example, dimethylamino, N-ethyl-N-methylamino or diethylamino.

A suitable value for $A^1$ when it is (1-4C)alkylene is, for example, methylene, ethylene, ethylidene, trimethylene, propylidene, propylene or tetramethylene; when it is (3-4C)alkenylene is, for example, 2-propenylene, 2-methylprop-2-enylene, 2-butenylene or 3-butenylene; and when it is (3-4C)alkynylene is, for example, 2-propynylene, 2-methylprop-2-ynylene, 2-butynylene or 3-butynylene.

A suitable value for Het when it is a 5- or 6-membered heteroaryl moiety containing up to 2 heteroatoms selected from nitrogen, oxygen and sulphur is, for example, a 5-membered heteroaryl moiety containing 1 heteroatom selected from nitrogen, oxygen and sulphur and optionally containing a further nitrogen heteroatom, or a 6-membered heteroaryl moiety containing 1 or 2 nitrogen heteroatoms. Convenient values for said heteroaryl moiety include, for example, pyrrolyl, furyl, thienyl, pyrazolyl, imidazolyl, oxazolyl, thiazolyl, pyridyl, pyridazinyl, pyrimidinyl and pyrazinyl. Any convenient linkage of said heteroaryl group to the groups $A^1$ and G is intended. Thus, for example, when Het is thienyl, a suitable value is 2,5-, 2,4- or 3,5-thiendiyl; and, for example, when Het is pyridyl, a suitable value is 2,4-, 2,5-, 2,6-, 3,5- or 3,6-pyriddiyl.

A suitable value for the substituent which may be present on Het when it is halogeno is, for example, fluoro, chloro or bromo; when it is (1-4C)alkyl is, for example, methyl, ethyl, propyl, isopropyl, butyl, isobutyl, sec-butyl or tert-butyl; and when it is (1-4C)alkoxy is, for example, methoxy, ethoxy, propoxy or isopropoxy.

A suitable value for $R^2$ when G is a group of the formula:

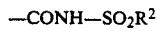

and $R^2$ is (1-4C)alkyl is, for example, methyl, ethyl, propyl or isopropyl.

When G is a group of the formula:

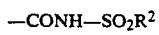

and $R^2$ is benzyl or phenyl which may optionally bear one or two substituents, a suitable value for said substituent when it is halogeno is, for example, fluoro, chloro or bromo; when it is (1-4C)alkyl is, for example, methyl, ethyl, propyl or isopropyl; and when it is (1-4C)alkoxy is, for example, methoxy, ethoxy, propoxy or isopropoxy.

A suitable value for an in-vivo hydrolysable ester of a tricyclic heterocycle of the formula I wherein G is carboxy is, for example, a pharmaceutically-acceptable ester which is hydrolysed in the human or animal body to produce the parent acid, for example, an ester formed with a (1-6C)alcohol such as methanol, ethanol, ethylene glycol, propanol or butanol, or with a phenol or benzyl alcohol such as phenol or benzyl alcohol or a substituted phenol or benzyl alcohol wherein the substituent is, for example, a halogeno (such as fluoro or chloro), (1-4C)alkyl (such as methyl) or (1-4C)alkoxy (such as methoxy) group.

A suitable value for an amide of a tricyclic heterocycle of the formula I wherein G is carboxy is, for example, a N-(1-6C)alkyl or N,N-di-(1-6C)alkyl amide such as a N-methyl, N-ethyl, N-propyl, N,N-dimethyl, N-ethyl-N-methyl or N,N-diethyl amide.

A suitable pharmaceutically-acceptable salt of a tricyclic heterocycle of the invention is, for example, an acid-addition salt of a tricyclic heterocycle of the invention which is sufficiently basic, for example an acid-addition salt with an inorganic or organic acid such as hydrochloric, hydrobromic, sulphuric or trifluoroacetic acid; or, for example a salt of a tricyclic heterocycle of the invention which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, tricyclic heterocycles of the formula I wherein:

(a) X is oxy, thio, sulphinyl or sulphonyl; and Y, $R^1$, m, n, $A^1$, Het and G have any of the meanings defined hereinbefore;

(b) X is oxy, thio, imino, (1-4C)alkylimino or methylene; and Y, $R^1$, m, n, $A^1$, Het and G have any of the meanings defined hereinbefore;

(c) X is oxy; and Y, $R^1$, m, n, $A^1$, Het and G have any of the meanings defined hereinbefore;

(d) Y is methylene optionally bearing one or two (1-4C)alkyl groups; and X, $R^1$, m, n, $A^1$, Het and G have any of the meanings defined hereinbefore;

(e) each $R^1$, which may be the same or different, is selected from hydrogen, halogeno, trifluoromethyl, nitro and cyano; and X, Y, m, n, $A^1$, Het and G have any of the meanings defined hereinbefore;

(f) each of m and n is the integer 1; and X, Y, $R^1$, $A^1$, Het and G have any of the meanings defined hereinbefore;

(g) $A^1$ is (1-4C)alkylene; and X, Y, $R^1$, m, n, Het and G have any of the meanings defined hereinbefore;

(h) Het is thienyl, thiazolyl or pyridyl; and X, Y, $R^1$, m, n, $A^1$ and G have any of the meanings defined hereinbefore;

(i) Het is 2,5-, 2,4- or 3,5-thiendiyl, 2,5- or 2,4-thiadiazolyl, or 2,4-, 2,5-, 2,6-, 3,5- or 3,6-pyriddiyl; and X, Y, $R^1$, m, n, $A^1$ and G have any of the meanings defined hereinbefore;

(j) G is carboxy or an in-vivo hydrolysable ester thereof; and X, Y, $R^1$, m, n, $A^1$ and Het have any of the meanings defined hereinbefore;

(k) G is 1H-tetrazol-5-yl; and X, Y, $R^1$, m, n, $A^1$ and Het have any of the meanings defined hereinbefore; and (l) G is a group of the formula:

wherein $R^2$ is (1-4C)alkyl or phenyl, the latter optionally bearing one or two substituents selected from halogeno, trifluoromethyl, nitro, cyano, hydroxy, (1-4C)alkyl and (1-4C)alkoxy; and X, Y, $R^1$, M, n, $A^1$ and Het have any of the meanings defined hereinbefore;
or a pharmaceutically-acceptable salt thereof.

A preferred compound of the invention comprises a tricyclic heterocycle of the formula I
wherein X is oxy, thio, amino, methylimino, ethylimino or methylene;
Y is carbonyl or Y is methylene optionally bearing one or two methyl or ethyl groups;
each $R^1$, which may be the same or different, is selected from hydrogen, fluoro, chloro, bromo, trifluoromethyl, nitro, cyano, methyl, ethyl, methoxy, ethoxy, methylthio, methylsulphinyl and methylsulphonyl; each of m and n is the integer 1;
$A^1$ is methylene, ethylene, ethylidene, trimethylene, propylidene, propylene, 2-propenylene or 2-propynylene;
Het is thienyl, thiazolyl or pyridyl which may optionally bear one substituent selected from fluoro, chloro, bromo, trifluoromethyl, nitro, cyano, hydroxy, amino, methyl, ethyl, methoxy and ethoxy; and G is carboxy, 1H-tetrazol-5-yl or a group of the formula:

$$-CONHSO_2R^2$$

wherein $R^2$ is methyl, ethyl or phenyl, the last group optionally bearing one substituent selected from fluoro, chloro, trifluoromethyl, nitro, cyano, hydroxy, methyl and methoxy;
or when G is carboxy an in-vivo hydrolysable ester thereof;
or a pharmaceutically-acceptable salt thereof.

A further preferred compound of the invention comprises a tricyclic heterocycle of the formula I
wherein X is oxy, thio or imino;
Y is methylene;
each $R^1$, which may be the same or different, is selected from hydrogen, chloro and trifluoromethyl;
each of m and n is the integer 1;
$A^1$ is methylene;
Het is 2,5-thiendiyl, 3,5-thiendiyl or 2,5-thiadiazoldiyl (with G in the 5-position in each case) or Het is 2,5-pyriddiyl (with G in the 5-position) or 2,6-pyriddiyl (with G in the 6-position), said heteroaryl moiety optionally bearing one substituent selected from fluoro, chloro or methyl; and
G is carboxy or an in-vivo hydrolysable ester thereof; or a pharmaceutically-acceptable salt thereof.

A further preferred compound of the invention comprises a tricyclic heterocycle of the formula I
wherein X is oxy or imino;
Y is methylene;
each $R^1$, which may be the same or different, is selected from hydrogen, chloro and trifluoromethyl;
each of m and n is the integer 1;
$A^1$ is methylene;
Het is 2,5-thiendiyl, 3,5-thiendiyl or 2,5-thiadiazoldiyl (with G in the 5-position in each case);
and G is carboxy or an in-vivo hydrolysable ester thereof; or a pharmaceutically-acceptable salt thereof.

A specific preferred compound of the invention is, for example, the following tricyclic heterocycle of the formula I, or an in-vivo hydrolysable ester thereof or a pharmaceutically-acceptable salt thereof:

5-(8-trifluoromethyl-10,11-dihydrodibenzo[b,f][1,4]oxazepin-10-ylmethyl)thiophene-2-carboxylic acid,
5-(11-oxo-10,11-dihydrodibenzo[b,e][1,4]diazepin-10-ylmethyl)thiophene-2-carboxylic acid,
4-(10,11-dihydrodibenzo[b,f][1,4]oxazepin-10-ylmethyl)thiophene-2-carboxylic acid, 5-(8-chloro-10,11-dihydrodibenzo[b,f][1,4]oxazepin-10-ylmethyl)-thiophene-2-carboxylic acid or
5-(10,11-dihydrodibenzo[b,e][1,4]diazepin-10-ylmethyl)thiophene-2-carboxylic acid.

A compound of the invention comprising a tricyclic heterocycle of the formula I, or when G is carboxy an in-vivo hydrolysable ester or an amide thereof, or a pharmaceutically-acceptable salt thereof, may be prepared by any process known to be applicable to the preparation of structurally-related compounds. Such procedures are provided as a further feature of the invention and are illustrated by the following representative process variants in which, unless otherwise stated, X, Y, $R^1$, m, n, $A^1$, Het and G have any of the meanings defined hereinbefore.

(a) The coupling of a compound of the formula II with a compound of the formula:

$$Z-A^1-Het-G$$

wherein Z is a displaceable group;
provided that any hydroxy, amino, imino, alkylamino or carboxy group in these reactants may be protected by a conventional protecting group or alternatively any such group need not be protected, whereafter any such protecting group is removed by conventional means.

A suitable displaceable group Z is, for example, a halogeno or sulphonyloxy group such as chloro, bromo, iodo, methanesulphonyloxy toluene-4-sulphonyloxy or trifluoromethylsulphonyloxy.

The coupling reaction is preferably carried out in the presence of a suitable base such as, for example, an alkali or alkaline earth metal carbonate, (1-4C)alkoxide, hydroxide or hydride, for example sodium carbonate, potassium carbonate, sodium ethoxide, potassium butoxide, sodium hydroxide, potassium hydroxide, sodium hydride or potassium hydride, or, for example, an organic amine base such as, for example, pyridine, lutidine, collidine, 4-dimethylaminopyridine, triethylamine, morpholine or diazabicyclo[5.4.0]undec-7-ene.

The coupling reaction is conveniently performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example −10° to 150° C., conveniently at or near ambient temperature.

Alternatively the coupling reaction may be performed utilising a phase transfer catalyst, for example a tetra-(1-4C)alkylammonium salt such as tetrabutylammoniwn hydroxide or hydrogen sulphate, a suitable alkali or alkaline earth metal hydroxide as defined above and a suitable inert solvent or diluent, for example methylene chloride or methyl ethyl ketone, and at a temperature in the range, for example 10° to 80° C., conveniently at or near ambient temperature.

A suitable protecting group for a hydroxy group is, for example, an arylmethyl group (especially benzyl), a tri-(1-4C)alkylsilyl group (especially trimethylsilyl or tert-butyldimethylsilyl), an aryldi-(1-4C)alkylsilyl group (especially dimethylphenylsilyl), a diaryl-(1-4C)alkylsilyl group (especially tert-butyldiphenylsilyl), a (1-4C)alkyl group (especially methyl), a (2-4C)alkenyl group (especially allyl), a (1-4C)alkoxymethyl group (especially methoxymethyl) or a tetrahydropyranyl group (especially tetrahydroyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, preferably, tetrabutylammonium fluoride. Alternatively an alkyl group may be removed, for example, by treatment with an alkali metal (1-4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1-4C)alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a (2-4C)alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a (2-4C)alkanoyl group (especially acetyl), a (1-4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1-4C)alkyl group (especially methyl or ethyl) which may be removed, for example, by hydrolysis with a suitable base such as an alkali metal hydroxide, for example lithium or sodium hydroxide; or, for example, a tert-butyl group which may be removed, for example, by treatment with a suitable acid such as hydrochloric, sulphuric or phosphoric acid or trifluoroacetic acid.

The starting materials of the formula II and of the formula:

$$Z-A^1-Het-G$$

may be obtained by standard procedures of organic chemistry. The preparation of such starting materials is described within the accompanying non-limiting Examples which are provided for the purpose of illustration only. Other necessary starting materials are obtainable by analogous procedures or by modifications thereto which are within the ordinary skill of an organic chemist.

(b) For the production of a compound of the formula I wherein Y is methylene, the reduction of a compound of the formula I wherein Y is carbonyl.

A suitable reducing agent is, for example, any agent known in the art for the reduction of the carbonyl group within an amide functional group to a methylene group. Many 'hydride' reducing agents can effect this reduction such as, for example, a borane reducing agent such as, for example, diborane. The reduction is preferably performed in a suitable inert solvent or diluent, for example an ether such as diethyl ether or tetrahydrofuran and at a temperature in the range, for example, 0° to 100° C., conveniently in the range 20° to 70° C.

(c) For the production of a compound of the formula I wherein $R^1$ is (1-4C)alkylthio, the displacement reaction of a compound of the formula I wherein $R^1$ is a displaceable substituent Z as defined hereinbefore with a (1-4C)alkylthiol.

The displacement reaction is preferably carried out in the presence of a suitable base as defined hereinbefore and in a suitable inert solvent or diluent, for example, N,N-dimethylformamide, N,N-dimethylacetamide, dimethylsulphoxide or N-methylpyrrolidin-2-one, at a temperature in the range, for example 100° C. to the boiling point of the solvent and in the presence of a copper catalyst, for example copper iodide.

(d) For the production of a compound of the formula I wherein $R^1$ is (1-4C)alkylsulphinyl or (1-4C)alkylsulphonyl, the oxidation of a compound of the formula I wherein $R^1$ is (1-4C)alkylthio.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as the corresponding thio compound.

(e) For the production of a compound of the formula I wherein G is a group of the formula $$-CONH-SO_2R^2$$

the reaction of a compound of the formula I wherein G is carboxy, or a reactive derivative thereof, with a sulphonamide of the formula:

$$H_2N-SO_2R^2$$

provided that any hydroxy, imino or alkylamino group in these reactants may be protected by a conventional protecting group or alternatively any such group need not be protected, whereafter any such protecting group is removed by conventional means.

A suitable reactive derivative of a compound of the formula I wherein G is carboxy is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an acyl azide, for example an azide formed by the reaction of the acid and an azide such as diphenylphophoryl azide; an acyl cyanide, for example a cyanide formed by the reaction of an acid and a cyanide such as diethylphosphoryl cyanide; or the product of the reaction of the acid and a carbodiimide, for example dicyclohexylcarbodiimide or 1-(3-dimethylaminopropyl)-3-ethylcarbodiimide.

The sulphonamidation reaction is preferably carried out in the presence of a suitable base as defined hereinbefore in a suitable solvent or diluent such as methylene chloride, N,N-dimethylformamide, N,N-dimethylacetamide or dimethylsulphoxide and at a temperature in the range, for example, 10° to 100° C., conveniently at or near ambient temperature.

When an in-vivo hydrolysable ester of a compound of the formula I wherein G is carboxy is required, it may be obtained, for example, by reaction of said compound of the formula I wherein G is carboxy, or a reactive derivative thereof as defined hereinbefore, with a suitable esterifying reagent using a conventional procedure.

When an amide of a compound of the formula I wherein G is carboxy is required, it may be obtained, for example, by reaction of said compound of the formula I wherein G is carboxy, or a reactive derivative thereof as defined hereinbefore, with a suitable amine using a conventional procedure.

When a pharmaceutically-acceptable salt of a compound of the formula I is required, it may be obtained, for example, by reaction of said compound with a suitable acid or base using a conventional procedure.

As stated hereinbefore a tricyclic heterocycle of the formula I possesses anti-hyperalgesic properties and hence is of value in the treatment of the hyperalgesic state which, for example, accompanies inflammatory conditions such as rheumatoid arthritis and osteoarthritis. These properties may be demonstrated using one or more of the test procedures set out below:

(a) an in-vitro guinea pig ileum assay which assesses the inhibitory properties of a test compound against $PGE_2$-induced contractions of the ileum; ileum was immersed in oxygenated Krebs solution containing indomethacin (4 $\mu$g/ml) and atropine (1 $\mu$M) and which was maintained at 37° C.; the ileum was subject to a tension of 1 g; a control dose response curve for $PGE_2$-induced contraction of the ileum was obtained; test compound (dissolved in dimethylsulphoxide) was added to the Krebs solution and a dose response curve for the $PGE_2$- induced contraction of the ileum in the presence of the test compound was obtained; the $pA_2$ value for the test compound was calculated;

(b) an in-vivo assay in mice which assesses the inhibitory properties of a test compound against abdominal constriction induced by the intraperitoneal administration of phenylbenzoquinone (hereinafter PBQ) using the procedure disclosed in European Patent Application No. 0218077.

Although the pharmacological properties of the compounds of the formula I vary with structural change as expected, in general activity possessed by compounds of the formula I may be demonstrated at the following concentrations or doses in one or more of the above-mentioned Tests (a) and (b):

Test (a):—$pA_2 > 5.3$;
Test (b):—$ED_{50}$ in the range, for example, 10–100 mg/kg orally.

Thus, by way of example, the compound 5-(8-chloro-10,11-dihydrodibenzo[b,f][1,4]oxazepin-10-ylmethyl)-thiophene-2-carboxylic acid has a $pA_2$ value of 7.5 in Test (a); and the compound 5-(10,11-dihydrodibenzo[b,e][1,4]diazepin-10-ylmethyl)thiophene-2-carboxylic acid has a $pA_2$ value of 7.6 in Test (a) and it possesses significant activity at 100 mg/kg in Test (b) on oral dosing.

No overt toxicity or other untoward effects were noted in Test (b) when compounds of the formula I are administered at several multiples of their minimum inhibitory dose.

Prostanoid receptors and in particular receptors for $PGE_2$ have been tentatively characterised by Kennedy et al. (Advances in Prostaglandin, Thromboxane and Leukotriene Research, 1983, 11, 327). The known $PGE_2$ antagonist SC-19220 blocks the effect of $PGE_2$ on some tissues such as guinea pig ileum or dog fundus but not on other tissues such as the cat trachea or chick ileum. Those tissues which did possess SC-19220 affected $PGE_2$ receptors were said to possess $EP_1$ receptors. Accordingly compounds of the present invention, possessing activity in Test (a), are $EP_1$ anatagonists.

According to a further feature of the invention there is provided a pharmaceutical composition which comprises a tricyclic heterocycle of the formula I, or when G is carboxy an in-vivo hydrolysable ester thereof or an amide thereof, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a tricyclic heterocycle of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a tricyclic heterocycle of the formula I, or when G is carboxy an in-vivo hydrolysable ester thereof or an amide thereof, or a pharmaceutically-acceptable salt thereof, for use in a method of treatment of the human or animal body by therapy.

According to a further feature of the invention there is provided the use of a tricyclic heterocycle of the formula I, or when G is carboxy an in-vivo hydrolysable ester thereof or an amide thereof, or a pharmaceutically-acceptable salt thereof, in the manufacture of a medicament for use in the production of an anti-hyperalgesic effect in the human or animal body.

According to a further feature of the invention there is provided a method for producing an anti-hyperalgesic effect in the human or animal body in need of such treatment which comprises administering to said body an effective amount of a tricyclic heterocycle of the formula I, or when G is carboxy an in-vivo hydrolysable ester thereof or an amide thereof, or a pharmaceutically-acceptable salt thereof.

As mentioned above, a tricyclic heterocycle of the formula I is useful in treating the hyperalgesic state which, for example, accompanies inflammatory conditions such as rheumatoid arthritis and osteoarthritis. In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to antagonise the effects of $PGE_2$. Thus, they are useful as pharmacological standards for use in the development of new biological tests and in the search for new pharmacological agents.

By virtue of their anti-hyperalgesic effect the compounds of the formula I are of value in the treatment of certain inflammatory diseases which are currently treated with a cyclooxygenase-inhibitory non-steroidal anti-inflammatory drug (NSAID) such as indomethacin, acetylsalicyclic acid, ibuprofen, sulindac, tolmetin and piroxicam. Co-administration of a compound of the formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a tricyclic heterocycle of the formula I, or when G is carboxy an in-vivo hydrolysable ester thereof or an amide thereof, or a pharmaceutically-acceptable salt thereof, in conjunction or admixture with a cyclooxygenase inhibitory non-steroidal anti-inflammatory agent, and a pharmaceutically-acceptable diluent or carrier.

The compositions of the invention may in addition contain one or more therapeutic or prophylactic agents known to be of value for the treatment of mild or moderate pain. Thus, for example, a known mild opiate pain-killer (such as dextropropoxyphene or codeine) or an inhibitor of the enzyme 5-lipoxygenase (such as those disclosed in European Patent Applications Nos. 0375404, 0385662, 0409413, 0420511, 0462812, 0462813) may usefully also be present in a pharmaceutical composition of the invention.

The invention will now be illustrated in the following non-limiting Examples in which, unless otherwise stated:

(i) evaporations were carried out by rotary evaporations in vacuo and work-up procedures were carried out after removal of residual solids by filtration;

(ii) operations were carried out at room temperature, that is in the range of 18°-20° C. and under an atmosphere of an inert gas such as argon;

(iii) column chromatography (by the flash procedure) and medium pressure liquid chromatography (MPLC) were performed on Merck Kieselgel silica (Art. 9385) obtained from E. Merck, Darmstadt, W. Germany;

(iv) yields are given for illustration only and are not necessarily the maximum attainable;

(v) the end-products of the formula I have satisfactory microanalyses and their structures were generally confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture; and (viii) the following abbreviations have been used:
DMF N,N-dimethylformamide;
THF tetrahydrofuran.

EXAMPLE 1

A solution of 8-trifluoromethyl-10,11-dihydrodibenzo[b,fl-[1,4]oxazepine (J. Med. Chem., 1968, 11, 1158; 2 g) in methylene chloride (20 ml) was added to a solution of tetrabutylammonium hydrogen sulphate (2.6 g) in 2N aqueous sodium hydroxide solution and the mixture was stirred at ambient temperature for 10 minutes. A solution of methyl 5-bromomethylthiophene-2-carboxylate (1.8 g) in methylene chloride (10 ml) was added and the mixture was stirred at ambient temperature for 18 hours. The organic layer was separated, washed with water (2×50ml), dried (MGSO$_4$) and evaporated. The residue was purified by column chromatography using a 1:1 v/v mixture of methylene chloride and hexane as eluent. There was thus obtained methyl 5-(8-trifluoromethyl-10,11-dihydrodibenzo[b,f][1,4]oxazepin-10-ylmethyl)thiophene-2-carboxylate (2.18 g), m.p. 81° C.

A mixture of the product so obtained, 2N aqueous sodium hydroxide solution (13.3 ml), THF (40 ml) and methanol (40 ml) was stirred at ambient temperature for 3 hours. The mixture was concentrated to approximately one half of its original volume by evaporation. The mixture was acidified by the addition of glacial acetic acid and the precipitate was isolated and dried. There was thus obtained 5-(8-trifluoromethyl-10,11-dihydrodibenzo[b,f][1,4]oxazepin-10-ylmethyl)thiophene-2-carboxylic acid (1.1 g), m.p. 185°–187° C.

The methyl 5-bromomethylthiophene-2-carboxylate used as a starting material was obtained from methyl 5-methylthiophene-2-carboxylate by conventional N-bromosuccinimide bromination in carbon tetrachloride using an analogous procedure to that described in *Tetrahedron*, 1967, 23, 2443. The methyl 5-methylthiophene-2-carboxylate was obtained by conventional esterification of 5-methylthiophene-2-carboxylic acid with methanol under acidic conditions.

EXAMPLE 2

Using a similar procedure to that described in Example 1, the appropriate 10,11-dihydrodibenzo[b,f][1,4]oxazepine was reacted with the appropriate bromomethyl compound and the resultant product was hydrolysed with aqueous sodium hydroxide solution. There were thus obtained the compounds described in Table I, the structures of which were confirmed by proton magnetic resonance and mass spectroscopy and by microanalysis.

TABLE I

[Structure: dibenzoxazepine with CH₂—Het—G substituent at N]

| Ex. 2 Compd. No. | Dibenzoxazepine Substituent | —Het—G | m.p. (°C.) |
|---|---|---|---|
| 1[a] | 8-chloro | 2-carboxythien-5-yl | 186 |
| 2[b] | 7-chloro | 2-carboxythien-5-yl | 167–169 |
| 3[c] | — | 2-carboxythien-4-yl | 182 |
| 4[d] | 8-chloro | 2-carboxypyrid-5-yl | 171 |
| 5[e] | — | 5-carboxypyrid-2-yl | 182 |
| 6 | 8-chloro | 5-carboxypyrid-2-yl | 204 |
| 7[f] | 8-chloro | 4-carboxythiazol-2-yl | 169–170 |

Notes

[a]The starting material 8-chloro-10,11-dihydrodibenzo[b,f]-[1,4]oxazepine is described in U.S. Pat. No. 3,357,998.
[b]The starting material 7-chloro-10,11-dihydrodibenzo[b,f]-[1,4]oxazepine was prepared via 7-chlorodibenzo[b,f][1,4]oxazepine which was prepared using analogous procedures to those described in J. Chem. Soc. Perkin I, 1976, 1279. The 7-chlorodibenzo[b,f][1,4]oxazepine was reduced with sodium borohydride using analogous procedures to those described in Coll. Czech. Chem. Comm., 1965, 30, 463.
[c]The starting material 10,11-dihydrodibenzo[b,f][1,4]oxazepine is described in Coll. Czech. Chem. Comm., 1965, 30, 463. The methyl 4-bromomethylthiophene-2-carboxylate used as a starting material is disclosed in Coll. Czech. Chem. Comm., 1974, 39, 3527 but it was obtained from 4-methylthiophene-2-carboxylic acid by the conventional steps of esterification with methanol under acidic conditions and bromination with N-bromosuccinimide in carbon tetrachloride.
[d]The methyl 5-bromomethylpyridine-2-carboxylate used as a starting material is described in Helv. Chim. Acta., 1975, 58, 682.
[e]The methyl 2-bromomethylpyridine-5-carboxylate used as a starting material was obtained from 2-methylpyridine-5-carboxylic acid by the conventional steps of esterification with methanol under acidic conditions and bromination with N-bromosuccinimide in carbon tetrachloride, with the exception that acetic acid (4% by volume) was added to the solvent in the latter step.
[f]Ethyl 2-bromomethylthiazole-4-carboxylate (Liebig's Annalen, TABLE I-continued 1981, 623) was used as one of the starting materials.

EXAMPLE 3

The procedures described in Example 1 were repeated except that 8-chloro-11-methyl-10,11-dihydrodibenzo[b,f][1,4]oxazepine was used in place of 8-trifluoromethyl-10,11-dihydrodibenzo[b,f][1,4]-oxazepine. There was thus obtained 5-(8-chloro-11-methyl-10,11-dihydrodibenzo[b,f][1,4]oxazepin-10-ylmethyl)thiophene-2-carboxylic acid in 20% yield, m.p. 135° C.

The starting material 8-chloro-11-methyl-10,11-dihydrodibenzo[b,f][1,4]oxazepine was obtained from 5'-chloro-2'-phenoxyacetanilide using analogous procedures to those described in *Coll. Czech. Chem. Comm.* 1965, 30, 463.

EXAMPLE 4

A solution of 8-chloro-10,11-dihydrodibenzo[b,f][1,4]-thiazepine (*Coll. Czech. Chem. Comm.*, 1959, 24, 207; 2 g) in DMF (20 ml) was added dropwise to a stirred suspension of sodium hydride (60% w/v dispersion in mineral oil, 0.38 g) in DMF (5 ml) which had been cooled to 0° C. The mixture was stirred at 0° C. for 30 minutes. A solution of methyl 5-bromomethylthiophene-2-carboxylate (1.89 g) in DMF (5 ml) was added dropwise. The mixture was allowed to warm to ambient temperature and was stirred for 18 hours. The mixture was poured onto ice and acidified by the addition of glacial acetic acid. The mixture was extracted with diethyl ether (3×50 ml). The combined extracts were washed with water and with brine, dried (MGSO₄) and evaporated. The residue was purified by column chromatography using a 3:2 v/v mixture of hexane and methylene chloride as eluent. There was thus obtained methyl 5-(8-chloro-10,11-dihydrodibenzo[b,f][1,4]thiazepin-10-ylmethyl)thiophene-2-carboxylate in 13% yield.

The product so obtained was hydrolysed using an analogous procedure to that described in the second paragraph of Example 1. There was thus obtained 5-(8-chloro-10,11-dihydrodibenzo[b,f][1,4]-thiazepin-10-ylmethyl)thiophene-2-carboxylic acid in 61% yield, m.p. 216°–217° C.

EXAMPLE 5

The procedures described in Example 4 were repeated except that 10,11-dihydro-5H-dibenzo[b,e][1,4]diazepin-11-one (*Synthesis*, 1985, 550) was used in place of 8-chloro-10,11-dihydrodibenzo[b,f]-[1,4]thiazepine. There was thus obtained 5-(11-oxo-10,11-dihydrodibenzo[b,e][1,4]diazepin-10-ylmethyl)thiophene-2-carboxylic acid in 25% yield, m.p. 225° C.

EXAMPLE 6

Diborane (1M in THF; 37 ml) was added to a stirred solution of methyl 5-(11-oxo-10,11-dihydrodibenzo[b,e][1,4]diazepin-10-ylmethyl)thiophene-2-carboxylate (4.5 g) in THF (100 ml). The mixture was stirred and heated to reflux for 6 hours. The mixture was allowed to cool to ambient temperature and glacial acetic acid (10 ml) was added. The mixture was partitioned between diethyl ether and water. The organic phase was washed with water and with brine, dried (MGSO₄) and evaporated. The residue was purified by column chromatography using methylene chloride as eluent. There was thus obtained methyl 5-(10,11-dihydrodibenzo[b,e][1,4]diazepin-10-ylmethyl)thiophene-2-carboxylate (2.2 g).

The product so obtained was hydrolysed using an analogous procedure to that described in the second paragraph of Example 1. There was thus obtained 5-(10,11-dihydrodibenzo[b,e][1,4]diazepin-10-ylmethyl)-thiophene-2-carboxylic acid in 55% yield, m.p. 125°–127° C.

EXAMPLE 7

The following illustrate representative pharmaceutical dosage forms containing the compound of formula I, or a pharmaceutically-acceptable salt thereof (hereafter compound X), for therapeutic or prophylactic use in humans:

| (a) | Tablet I | mg/tablet |
|---|---|---|
| | Compound X | 100 |
| | Lactose Ph. Eur. | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph. Eur. | 223.75 |
| | Croscarmellose sodium | 6.0 |
| | Maize starch | 15.0 |
| | Polyvinylpyrolidone (5% w/v paste) | 2.25 |
| | Magnesium stearate | 3.0 |
| (c) | Tablet III | mg/tablet |
| | Compound X | 1.0 |
| | Lactose Ph. Eur. | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph. Eur. | 488.5 |
| | Magnesium stearate | 1.5 |
| (e) | Injection I | (50 mg/ml) |
| | Compound X | 5.0% w/v |
| | 1M Sodium hydroxide solution | 15.0% w/v |
| | 0.1M Hydrochloric acid (to adjust pH to 7.6) | |
| | Polyethylene glycol 400 | 4.5% w/v |
| | Water for injection to 100% | |
| (f) | Injection II | (10 mg/ml) |
| | Compound X | 1.0% w/v |
| | Sodium phosphate BP | 3.6% w/v |
| | 0.1M Sodium hydroxide solution | 15.0% v/v |
| | Water for injection to 100% | |
| (g) | Injection III | 1 mg/ml, buffered to pH 6 |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |
| (h) | Aerosol I | mg/ml |
| | Compound X | 10.0 |
| | Sorbitan trioleate | 13.5 |
| | Trichlorofluoromethane | 910.0 |
| | Dichlorodifluoromethane | 490.0 |
| (i) | Aerosol II | mg/ml |
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |
| (j) | Aerosol III | mg/ml |
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |
| (k) | Aerosol IV | mg/ml |
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

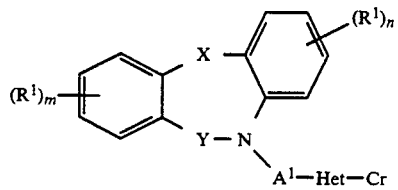

I

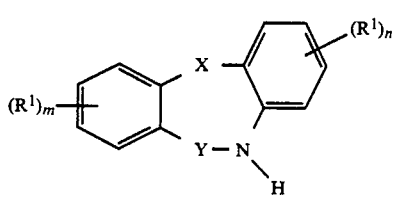

II

We claim:

1. A compound of the formula I

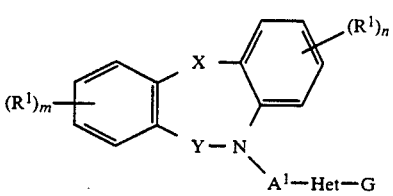

wherein

X is oxy, thio, sulphinyl, imino, (1-4C) alkylamino or methylene, the last named group optionally bearing one or two (1-4C) alkyl groups;

Y is carbonyl or methylene, the latter group optionally bearing one or two (1-4C)alkyl groups;

each $R^1$ which may be the same or different, is selected from hydrogen, halogeno, trifluoromethyl, nitro, cyano, hydroxy, amino, (1-4C)alkyl, (1-4C)alkoxy, (1-4C)alkylthio, (1-4C)alkylsulphinyl, (1-4C)alkylsulphonyl, (1-4C)alkylamino and di-(1-4C)alkylamino;

m and n, which may be the same or different, is the integer 1 or 2;

$A^1$ is (1-4C)alkylene, (3-4C)alkenylene or (3-4C)alkynylene;

Het is a 5- or 6-membered heteroaryl moiety containing up to 1 heteroatom selected from nitrogen, oxygen and sulphur and optionally containing a further nitrogen heteroatom, or a 6-membered heteroaryl moiety containing 1 or 2 nitrogen heteroatoms, and which may optionally bear one substituent selected from halogeno, trifluoromethyl, nitro, cyano, hydroxy, amino, (1-4C)alkyl and (1-4C)alkoxy; and G is carboxy, 1H-tetrazol-5-yl or a group of the formula:

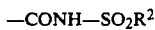
—CONH—SO$_2$R$^2$ wherein R$^2$ is (1-4C)alkyl, benzyl or phenyl, the latter two of which may optionally bear one or two substituents selected from halogeno, trifluoromethyl, nitro, cyano, hydroxy, (1-4C)alkyl and (1-4C)alkoxy; or when G is carboxy an in-vivo hydrolysable ester thereof or an amide thereof;

or a pharmaceutically-acceptable salt thereof.

2. A compound according to claim 1 wherein X is oxy, thio, amino, methylimino, ethylimino or methylene;

Y is carbonyl or Y is methylene optionally bearing one or two methyl or ethyl groups;

each R$^1$, which may be the same or different, is selected from hydrogen, fluoro, chloro, bromo, trifluoromethyl, nitro, cyano, methyl, ethyl, methoxy, ethoxy, methylthio, methylsulphinyl and methylsulphonyl;

each of m and n is the integer 1;

A$^1$ is methylene, ethylene, ethylidene, trimethylene, propylidene, propylene, 2-propenylene or 2-propynylene;

Het is thienyl, thiazolyl or pyridyl which may optionally bear one substituent selected from fluoro, chloro, bromo, trifluoromethyl, nitro, cyano, hydroxy, amino, methyl, ethyl, methoxy and ethoxy; and G is carboxy, 1H-tetrazol-5-yl or a group of the formula:

—CONHSO$_2$R$_2$ wherein R$^2$ is methyl, ethyl or phenyl, the last group optionally bearing one substituent selected from fluoro, chloro, trifluoromethyl, nitro, cyano, hydroxy, methyl and methoxy;

or when G is carboxy an in-vivo hydrolysable ester thereof;

or a pharmaceutically-acceptable salt thereof.

3. A compound according to claim 1 wherein X is oxy,-thio or imino;

Y is methylene;

each R$^1$ which may be the same or different, is selected from hydrogen, chloro and trifluoromethyl;

each of m and n is the integer 1;

A$^1$ is methylene;

Het is 2,5-thiendiyl, 3,5-thiendiyl or 2,5-thiadiazoldiyl (with G in the 5-position in each case) or Het is 2,5-pyriddiyl (with G in the 5-position) or 2,6-pyriddiyl (with G in the 6-position), said heteroaryl moiety optionally bearing one substituent selected from fluoro, chloro or methyl; and G is carboxy or an in-vivo hydrolysable ester thereof;

or a pharmaceutically-acceptable salt thereof.

4. A compound according to claim 1 wherein X is oxy or imino;

Y is methylene;

each R$^1$, which may be the same or different, is selected from hydrogen, chloro and trifluoromethyl;

each of m and n is the integer 1;

A$^1$ is methylene;

Het is 2,5-thiendiyl, 3,5-thiendiyl or 2,5-thiadiazoldiyl (with G in the 5-position in each case);

and G is carboxy or an in-vivo hydrolysable ester thereof;

or a pharmaceutically-acceptable salt thereof.

5. A compound according to claim 1 which is:
5-(8-trifluoromethyl-10,11-dihydrodibenzo[b,f][1,4]oxazepin-10-ylmethyl)thiophene-2-carboxylic acid,
5-(11-oxo-10,11-dihydrodibenzo[b,e][1,4]diazepin-10-ylmethyl)thiophene-2-carboxylic acid,
4-(10,11-dihydrodibenzo[b,f][1,4]oxazepin-10-ylmethyl)thiophene-2-carboxylic acid,
5-(8-chloro-10,11-dihydrodibenzo[b,f][1,4]oxazepin-10-ylmethyl)thiophene-2-carboxylic acid or
5-(10,11-dihydrodibenzo[b,e][1,4]diazepin-10-ylmethyl)thiophene-2-carboxylic acid:
or an in-vivo hydrolysable ester thereof or a pharmaceutically-acceptable salt thereof.

* * * * *